US00PP23354P3

(12) United States Plant Patent
Meilland

(10) Patent No.: US PP23,354 P3
(45) Date of Patent: Jan. 29, 2013

(54) FLORIBUNDA ROSE PLANT NAMED 'MEIMIRROTE'

(50) Latin Name: *Rosa hybrida*
Varietal Denomination: Meimirrote

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 296 days.

(21) Appl. No.: 12/662,244

(22) Filed: Apr. 7, 2010

(65) Prior Publication Data

US 2011/0252513 P1 Oct. 13, 2011

(51) Int. Cl.
*A01H 5/00* (2006.01)

(52) U.S. Cl. ..... Plt./148

(58) Field of Classification Search ..... Plt./148
See application file for complete search history.

(56) References Cited

U.S. PATENT DOCUMENTS

PP14,274 P2 * 11/2003 Meilland ..... Plt./118
2011/0252513 P1 * 10/2011 Meilland ..... Plt./148

OTHER PUBLICATIONS

Anonymous. "Apricot Drift" *Rosa* Meimirrote. Available at http://www.conard-pyle.com/index.cfm/fuseaction/drplants.plantDetail/plant_id/970/index accessed Jul. 13, 2011.*

Anonymous. "MEImirrot rose" available at Http://www.helpmefind.com/gardening/1.php?1=2.61451.1&tab=1.*

* cited by examiner

*Primary Examiner* — Wendy C Haas

(74) *Attorney, Agent, or Firm* — Buchanan Ingersoll & Rooney

(57) ABSTRACT

A new and distinct Floribunda rose plant is provided which abundantly forms on a substantially continuous basis attractive very double blossoms having a light pink coloration. The plant exhibits very strong, very dense vegetation, a bushy low to arching growth habit, and attractive green foliage with a glossy aspect. The disease resistance is good particularly with respect to Black Spot and *Oidium*. The attractive green foliage contrasts nicely with the light pink blossom coloration. The new variety is well suited for growing as attractive ornamentation in parks and gardens.

2 Drawing Sheets

Figure 1:
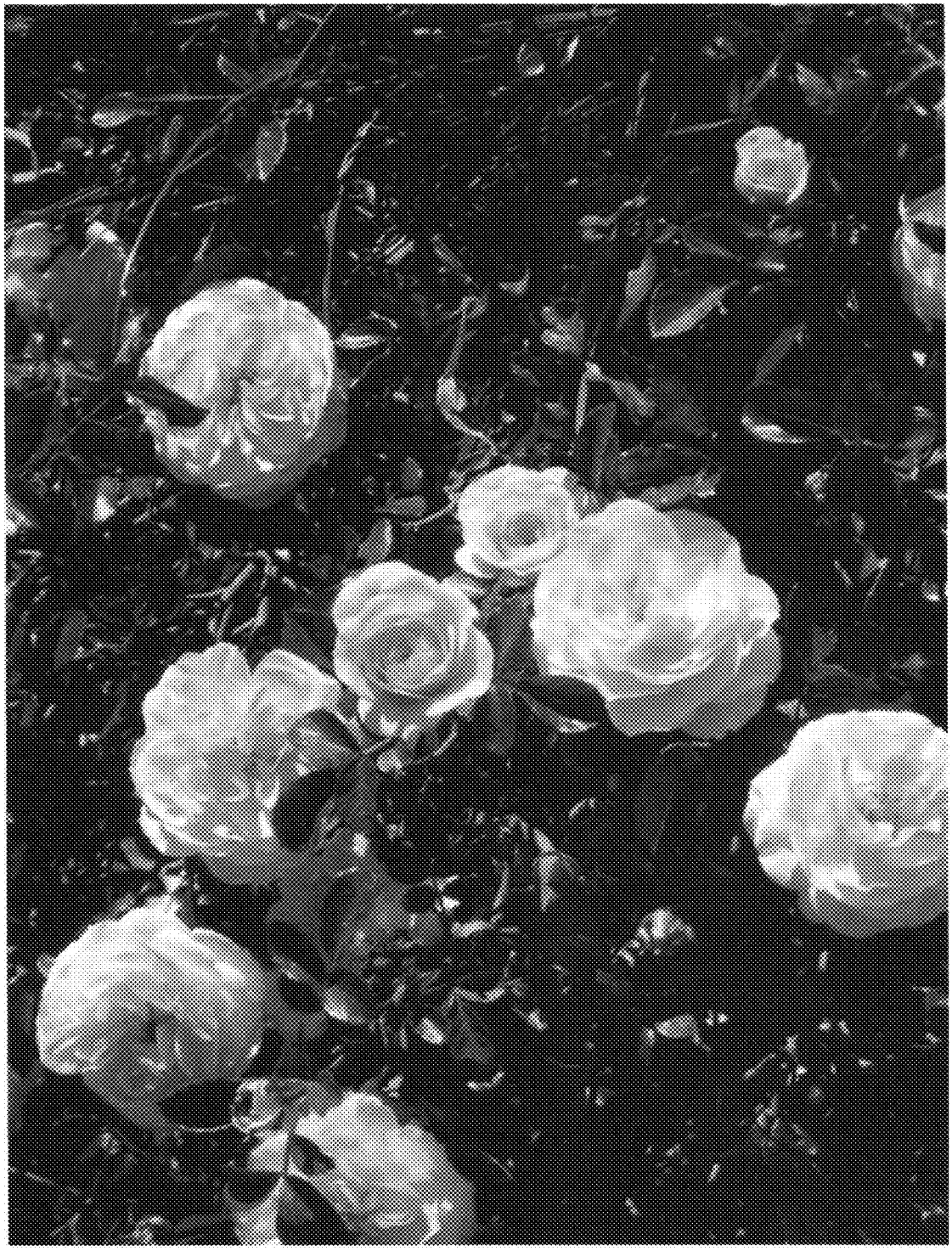

Botanical/commercial classification: *Rosa hybrida*/Floribunda Rose Plant.

Varietal denomination: cv. Meimirrote.

SUMMARY OF THE INVENTION

The new variety of *Rosa hybrida* Floribunda rose plant was created by artificial pollination wherein two parents were crossed which previously had been studied in the hope that they would contribute the desired characteristics. The female parent (i.e., the seed parent) was the 'The Fairy' variety (non-patented in the United States). The male parent (i.e., the pollen parent) was the product of the cross of the 'Korwest' variety (non-patented in the United States) and 'Meiskaille' variety (U.S. Plant Pat. No. 14,274). The parentage of the new variety can be summarized as follows:

'The Fairy'×('Korwest'×'Meiskaille').

The seeds resulting from the above pollination were sown and small plants were obtained which were physically and biologically different from each other. Selective study resulted in the identification of a single plant of the new variety.

It was found that the new Floribunda rose plant of the present invention:

(a) exhibits a bushy low to arching growth habit,
(b) abundantly forms on a substantially continuous basis attractive very double blossoms having a light pink coloration,
(c) forms very strong, very dense vegetation with attractive green foliage having a glossy aspect, (d) displays good disease resistance with respect to Black Spot and *Oidium*, and
(e) is well suited for growing as ornamentation in parks and gardens.

The attractive green foliage contrasts nicely with the light pink blossom coloration.

The new variety well meets the needs of the horticultural industry and can be grown to advantage in the landscape where attractive ornamentation is desired.

The new variety can be readily distinguished from its ancestors. For instance, 'The Fairy' variety displays blossoms having a pale rose coloration, the 'Korwest' variety displays a dissimilar climbing growth habit, and the 'Meiskaille' variety displays blossoms having a yellow coloration.

The new variety also can be readily distinguished from other similar rose varieties, such as the 'Meiggili' variety (U.S. Plant Pat. No. 18,542). More specifically, the 'Meiggili' variety displays bright peach blossoms with fragrance while those of the new variety are light pink in coloration and lack fragrance.

The new variety has been found to undergo asexual propagation at Le Luc, France by a number of routes, including budding, grafting, and the use of cuttings. Asexual propagation by the above-mentioned techniques has shown that the characteristics of the new variety are stable and are strictly transmissible by such asexual propagation from one generation to another. Accordingly, the new variety undergoes asexual propagation in a true-to-type manner.

The new variety has been named 'Meimirrote'.

BRIEF DESCRIPTION OF THE PHOTOGRAPHS

The accompanying photographs show as nearly true as it is reasonably possible to make the same, in color illustrations of this character, typical specimens of the new variety. The rose plants of the new variety were approximately two years of age and were observed during October while budded on *Rosa froebelii* understock (non-patented in the United States) and growing outdoors at Le Luc, Le Cannet des Maures, Var, France.

Figure 2:
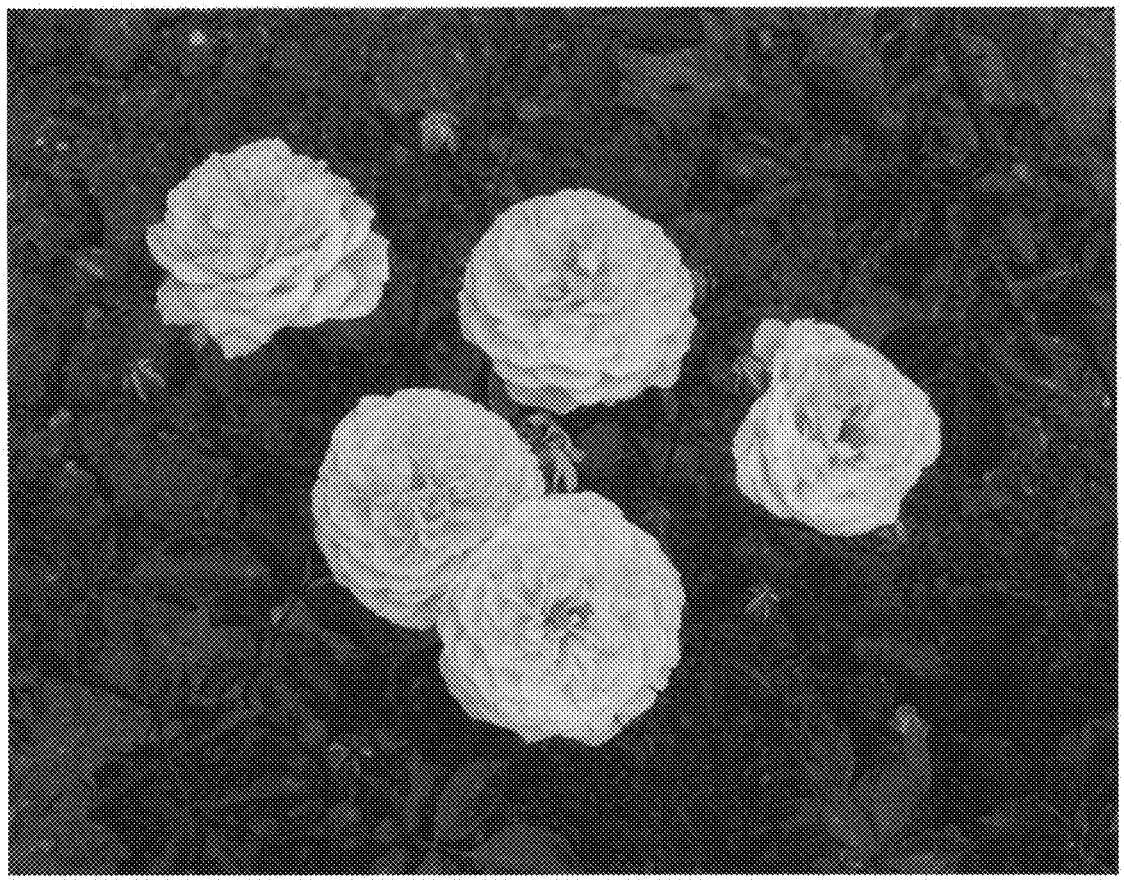

FIG. 1 illustrates typical blossoms in various stages of opening and the attractive glossy foliage of the new variety, and FIG. 2 illustrates a closer view of fully open blossoms of the new variety.

DETAILED DESCRIPTION

Common color terms are to be accorded their customary dictionary significance. The description is based on the observation of two-year-old plants during October while budded on *Rosa froebelii* understock and growing outdoors at Le Luc, Le Cannet des Maures, Var, France. Color designations are provided by reference to The R.H.S. Colour Chart (1995 Edition or equivalent) of The Royal Horticultural Society, London, England.

Class: Floribunda.

Plant:

*Habit*.—Bushy, low to arching.

*Height*.—Approximately 35 to 40 cm on average.

*Width*.—Approximately 35 to 40 cm on average.

Leaves:

*Length*.—Approximately 7.8 cm on average for a five-leaflet leaf.

*Width*.—Approximately 5.5 cm on average for a five-leaflet leaf.

*Leaflets*.—Number 3, 5, and 7. shape: generally oval with a rounded base and a somewhat cuspidate tip. general appearance: very dense with a glossy upper surface. length: approximately 3 cm for a mature terminal leaflet. width: approximately 2.4 cm for a mature terminal leaflet. color on upper surface: near Green Group 137A. color on under surface: near Green Group 137C. margin: denticulate. serration: single and small. texture: generally smooth on both surfaces without pubescence. venation: commonly near Green Group 137D on the upper surface and on the under surface.

*Stipules*.—Shape: rather broad. length: commonly approximately 0.4 cm on average. width: commonly approximately 0.4 cm on average. color on upper surface: commonly near Green Group 138B and lacking anthocyanin coloration. color on under surface: commonly near Yellow-Green Group 146C and lacking anthocyanin coloration.

Inflorescence:

*Number of flowers*.—Commonly approximately 3 to 12 per stem.

*Buds*.—Shape: globular. size: small. length: approximately 1.3 cm on average. color as the calyx breaks: on both surfaces commonly near Orange Group 27A suffused with near Orange Group 29C.

*Flower*.—Shape: cup-shaped. diameter: approximately 5 to 7 cm on average. color (when first opening): upper surface: near Orange Group 27A amply suffused with near Orange Group 29C. under surface: near Orange Group 27D. color (when fully open): upper surface: near Orange Group 27D amply suffused with near Red Group 38C. under surface: near Orange Group 29D amply suffused with near Red Group 38C. color (base spot): near Yellow Group 5B on upper and under surfaces. fragrance: none. petal number: commonly approximately 50 to 55 on average under normal growing conditions. petaloids: none observed. lastingness: commonly approximately 15 days on the plant. Not evaluated in a vase since this is primarily a garden variety. petal drop: good with the petals commonly detaching cleanly before drying.

Development:

*Vegetation*.—Very strong.

*Blooming*.—Very abundant, and substantially continuous.

*Resistance to diseases*.—Very good, particularly with respect to Black Spot and *Oidium*.

*Resistance to heat*.—Has withstood summer temperatures of 40° C. at Le Luc, Le Cannet Des Maures, Var, France.

*Resistance to cold*.—Has withstood winter temperatures of −15° C. at Le Luc, Le Cannet Des Maures, Var, France.

I claim:

1. A new and distinct Floribunda rose plant characterized by the following combination of characteristics:

(a) exhibits a bushy low to arching growth habit, (b) abundantly forms on a substantially continuous basis attractive very double blossoms having light pink coloration, (c) forms very strong, very dense vegetation with attractive green foliage having a glossy aspect, (d) displays good disease resistance with respect to Black Spot and *Oidium*, and (e) is well suited for growing as ornamentation in parks and gardens; substantially as herein shown and described.

* * * * *